US00RE37474B1

(19) United States
(12) Reissued Patent
Hug et al.

(10) Patent Number: US RE37,474 E
(45) Date of Reissued Patent: Dec. 18, 2001

(54) ADJUSTABLE DUAL-DETECTOR IMAGE DATA ACQUISITION SYSTEM

(75) Inventors: Paul Hug, Saratoga; Horace H. Hines; Mark L. Lamp, both of San Jose, all of CA (US)

(73) Assignee: ADAC Laboratories, Milpitas, CA (US)

(21) Appl. No.: 08/916,985

(22) Filed: Aug. 21, 1997

Related U.S. Patent Documents

Reissue of:
(64) Patent No.: 5,444,252
Issued: Aug. 22, 1995
Appl. No.: 08/154,239
Filed: Nov. 18, 1993

U.S. Applications:

(63) Continuation-in-part of application No. 07/704,759, filed on May 23, 1991, now Pat. No. 6,184,530.

(51) Int. Cl.[7] ..... G01T 1/164; G01T 1/166
(52) U.S. Cl. ..... 250/363.08; 250/363.05
(58) Field of Search ..... 250/363.08, 363.04, 250/363.05; 378/15

(56) References Cited

U.S. PATENT DOCUMENTS

| | | | | |
|---|---|---|---|---|
| H12 | * | 1/1986 | Bennett et al. | 250/363.02 |
| Re. 29,216 | | 5/1977 | Colombo et al. . | |
| 1,599,696 | | 9/1926 | Wantz . | |
| 2,595,260 | | 5/1952 | Hollstein . | |
| 3,011,057 | | 11/1961 | Anger . | |

(List continued on next page.)

FOREIGN PATENT DOCUMENTS

| | | | |
|---|---|---|---|
| 2070464 | 6/1992 | (CA) | A61B/6/02 |
| 314543A1 | 11/1981 | (DE) | G01T/1/29 |
| 0332937A1 | 3/1989 | (EP) | A61B/6/00 |
| 465952A2 | 6/1991 | (EP) | G01T/1/164 |
| 1175032 | 3/1967 | (FR) | B65H/57/04 |
| 1572809 | 12/1975 | (GB) | G01T/1/202 |
| 2120060A | 4/1983 | (GB) | A61B/6/00 |
| 61207978 | 3/1985 | (JP) | G01T/1/164 |
| 61-83984 | 4/1986 | (JP) . | |
| 62-5193 | 1/1987 | (JP) . | |
| 62-145181 | 6/1987 | (JP) . | |
| 64-9390 | 1/1989 | (JP) . | |
| 4256885 | 2/1991 | (JP) | G01T/1/164 |
| 1540365 | 9/1977 | (NL) | G01N/23/06 |
| WO9207512 | 10/1991 | (WO) | A61B/6/03 |

OTHER PUBLICATIONS

U.S. Statutory Invention Registration, H12, "Nuclear Medicine Imaging System," Gerald W. Bennett, et al., Published Jan. 7, 1986.

Stefan P. Mueller et al., "Collimator Selection for SPECT Brain Imaging: The Advantage of High Resolution," The Journal of Nuclear Medicine, vol. 27, No. 11, Nov. 1986, pp. 1729–1738.

(List continued on next page.)

*Primary Examiner*—Georgia Epps
*Assistant Examiner*—Richard Hanig
(74) *Attorney, Agent, or Firm*—Jordan M. Becker

(57) ABSTRACT

An improved image acquisition system allows the angular displacement between two detectors to be adjusted between 90° and 180° to reduce the imaging time for both 360° and 180° scans. A patient table is displaced vertically and horizontally from a lateral axis to allow the body of a patient to be positioned next to the detectors and to improve resolution.

13 Claims, 13 Drawing Sheets

U.S. PATENT DOCUMENTS

| | | | | |
|---|---|---|---|---|
| 3,281,598 | | 10/1966 | Hollstein . | |
| 3,549,885 | | 12/1970 | Anderson . | |
| 3,617,749 | | 11/1971 | Massiot . | |
| 3,697,751 | | 10/1972 | Tschunt . | |
| 3,735,132 | | 5/1973 | Carugati et al. . | |
| 3,756,549 | | 9/1973 | Lange . | |
| 3,845,308 | | 10/1974 | Cattrell . | |
| 3,852,601 | | 12/1974 | Casale . | |
| 3,870,886 | | 3/1975 | Casale . | |
| 3,976,885 | | 8/1976 | Brunnett et al. . | |
| 4,049,966 | | 9/1977 | Luitwieler, Jr. . | |
| 4,057,727 | | 11/1977 | Muehllehner et al. . | |
| 4,064,441 | | 12/1977 | Casale . | |
| 4,150,297 | | 4/1979 | Borggren . | |
| 4,190,772 | * | 2/1980 | Dinwiddie et al. | 250/445 T |
| 4,216,381 | | 8/1980 | Lange . | |
| 4,220,890 | | 9/1980 | Beekmans . | |
| 4,223,222 | | 9/1980 | Gray et al. . | |
| 4,298,801 | | 11/1981 | Heitman et al. . | |
| 4,400,620 | | 8/1983 | Blum . | |
| 4,401,890 | | 8/1983 | Blum . | |
| 4,426,725 | | 1/1984 | Grady . | |
| 4,445,035 | | 4/1984 | Ueyama . | |
| 4,476,389 | | 10/1984 | Ueyama et al. . | |
| 4,503,331 | | 3/1985 | Kovacs, Jr. et al. . | |
| 4,613,122 | | 9/1986 | Manabe . | |
| 4,645,933 | | 2/1987 | Gambini et al. . | |
| 4,652,758 | | 3/1987 | Barfod . | |
| 4,652,759 | | 3/1987 | Platz . | |
| 5,206,512 | | 4/1993 | Iwao . | |
| 5,349,190 | | 9/1994 | Hines et al. . | |

OTHER PUBLICATIONS

Robert L. Eisner, "Principles of Instrumentation in SPECT," Journal of Nuclear Medicine Technology, vol. 13, No. 1, Mar. 1995, pp. 23–31.

John W. Keyes, Jr., M.D., "Computed Tomography in Nuclear Medicine," Lieberman, D.E., Computer Methods, C.V. Mosby Co., St. Louis, 1977, pp. 130–138.

Lim et al., "Performance Analysis of Three Camera Configurations for Single Photon Emission Computer Tomography," IEEE Transactions on Nuclear Science, Feb. 1980, pp. 559–568.

Stoddart et al., "A New Development in Single Gamma Transaxial Tomography Union Carbide Focused Collimator Scanner," IEEE Transactions on Nuclear Science, 1979, pp. 2710–2712.

Gottschalk et al., "SPECT Resolution and Uniformity Improvements by Noncircular Orbit," The Journal of Nuclear Medicine, vol. 24, No. 9, 1983, pp. 822–828.

* cited by examiner

ADJUSTABLE DUAL-DETECTOR IMAGE DATA ACQUISITION SYSTEM

Matter enclosed in heavy brackets [ ] appears in the original patent but forms no part of this reissue specification; matter printed in italics indicates the additions made by reissue.

This application is a continuation-in-part of Ser. No. 07/704,759, filed May 23, 1991 *U.S. Pat. No. 6,184,530*.

BACKGROUND OF THE INVENTION

1. Field of the Invention

The present invention relates generally to imaging systems and more particularly to imaging systems for use in nuclear medicine.

2. Description of the Relevant Art

Gamma ray cameras are used in nuclear medicine to generate high quality images for brain, SPECT (Single Photon Emission Computer Tomograph), and total body bone studies. These cameras are most frequently used for cardiac and total body bone studies.

It is very important that the gamma ray camera be designed for high patient throughput for both economic and therapeutic reasons. The cost for diagnosing each patient is reduced if more patients can be diagnosed per unit time. For very sick patients or patients in intensive care it is important to minimize the time required to acquire image data. Patient throughput is increased if imaging time is reduced. Other factors, such as patient set-up time also affect patient throughput.

Modern gamma ray cameras utilize detectors, such as Anger cameras, having a wide field of view so that it is possible to image the full width of the body of a patient at each angular stop without the requirement of rectilinear scanning. These detectors use thick lead collimators to focus images and are thus very heavy. The collimators must be positioned as close to the patient as possible to acquire image data required to generate high resolution images. The image data acquired by the detectors is processed by a computer to generate an image. Techniques for processing image data are well-know in the art and described in "Principles of Instrumentation in SPECT" by Rober Eisner, Journal of Nuclear Medicine, Vol. 13, #1, March 1985, pp. 23–31; Computed Tomography in Nuclear Medicine" by John Keyes, (chapter in) Computer Methods, C. V. Mosley, St. Louis, 1977, pp. 130–138; and "Single Photon Emission Computed Tomography," by Bernard Oppenheim and Robert Appledown, (chapter in) Effective Use of Computers in Nuclear Medicine, Michael Gelfand and Stephen Thomas, McGraw-Hill Book Co., New York 1988, pp. 31–74.

Recent technological innovations have produced dual-head systems, with two detectors having their detector image direction arrows oriented at a fixed angle of 180°, and triple-head systems, with three detectors having their image direction arrows oriented at fixed angles of 120°, SPECT gamma ray cameras capable of rapid, high quality SPECT imaging. FIGS. 1A and 1B are schematic diagrams depicting the fixed orientation of the detector image direction arrows 2 of the detectors 4 in a dual-head and triple-head system.

When the detectors rotate about the patient, a lateral axis is defined as the mechanical axis of rotation aligned with the computer matrix for reconstructing the SPECT images.

The single, dual, and triple head cameras each have certain features which are advantageous for a particular type of application. To determine which system is best for a particular application factors such as 1) the ability of the camera to perform required imaging tasks; 2) the quality of the images generated; and 3) patient throughput should be considered.

The acquisition of data for a total body scan requires movement of the detector along the length of the patient's body. The dual-head system is very efficient because image data for anterior/posterior images can be acquired simultaneously. The time required to complete a scan can be reduced from 45 to 60 minutes, for a single-head camera, to 30 minutes. The triple-head system is no more efficient than the single-head system because the detectors cannot be aligned to acquire simultaneous anterior/posterior or left/right lateral data.

To generate high-quality SPECT for brain, bone, or liver studies views taken along a complete 360° circle (360° scan) around the body of the patient are required. Typically, about 64 to 128 angular stops are required to acquire the image data. The above-described dual-head camera reduces the imaging time to ½ the imaging time of a single-head system because data is acquired from two stops simultaneously. The triple-head camera reduces the imaging time to about ⅓ the imaging time of a single-head system because data is acquired from three stops simultaneously.

For cardiac SPECT studies, the analysis of complex imaging considerations has led to the use of at least 32 stops over a 180° arc about the patient's body (180° scan). For a 180° scan the imaging time of a single-head and dual-head system are the same because only one detector of the dual-head system is within the 180° arc at any given time. A triple-head system reduces the image time to about ⅔ the time of a single-head system for a 180° scan because two detectors are within the 180° arc about ⅓ of the time.

In view of the above it is apparent that the mechanical system for orienting the detectors must be designed to provide a mechanism for accurately orienting the detectors at various angular stops relative to the patient and to position the collimator as close to the patient as possible. Additionally, the system must be stable so that the heavy detectors are held still at each stop to facilitate the acquisition of accurate imaging data. Other attributes that are required of the mechanical system are ease of patient positioning, size of footprint, and overall size.

Further, as described above, the existing systems each have advantages for particular applications but generally lack the flexibility for optimal performance over a range of applications. Additionally, although cardiac SPECT imaging accounts for about 33% of the use of gamma ray cameras, none of the systems significantly reduce the imaging time for the 180° scan used in forming cardiac SPECT images.

SUMMARY OF THE INVENTION

The present invention is a unique system for reducing the imaging time required to generate a 180° SPECT image.

According to one aspect of the invention, the angular displacement between two detectors may adjusted to any angle between about 90° and 180° and the detectors can be rotated to any desired angular position along a circular path centered on a lateral axis. Thus, the system can be optimally configured for total body scans and 360° SPECT (relative angular displacement of 180°) and 180° SPECT (relative angular displacement of 90°) to provide a very flexible system.

According to a further aspect of the invention, each detector can be independently rotated along different circular paths centered on the lateral axis.

According to another aspect of the invention, both detectors are coupled to a single pair of rings. Each of the rings has an arc shaped groove which is substantially parallel to the circumference of the ring and aligned with the arc-shaped groove in the other ring. The second detector is coupled to the groove via guide rollers mounted to a support arm attached to the second detector which allows the second detector to move along the groove so as to vary the lateral displacement, relative to the lateral axis, between the first and second detectors to a selected magnitude having a value of between 90° and 180°.

According to another aspect of the invention, each detector is separately coupled to a first and second pair of rings respectively. Each of the first pair of rings has a radial support flange that is integral with and perpendicular to the inner surface of each of the first pair of rings. The second pair of rings is positioned on the radial support flange of each of the first pair of rings so that the second pair of rings is displaced laterally away from the first pair of rings and is disposed between the first pair of rings. The second pair of rings may be rotated independent of the first pair of rings to adjust the angular displacement between the detectors to a predetermined magnitude.

According to another aspect of the invention, each detector may be independently moved toward or away from the lateral axis.

Other features and advantages of the invention will be apparent in view of the appended figures and following detailed description.

DESCRIPTION OF THE PREFERRED EMBODIMENT

Figure 1A:
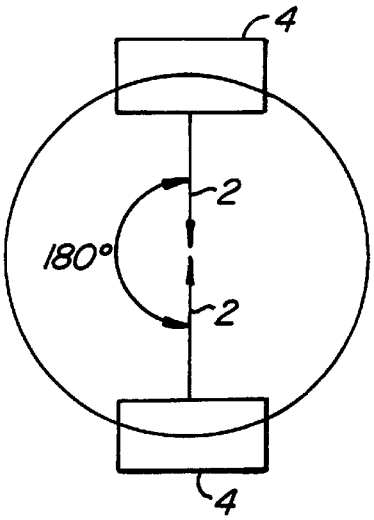
FIG. 1A. PRIOR ART
FIGS. 1A and 1B are schematic views depicting the fixed orientation of the detectors for existing dual-head and triple head imaging systems.
Figure 1B:
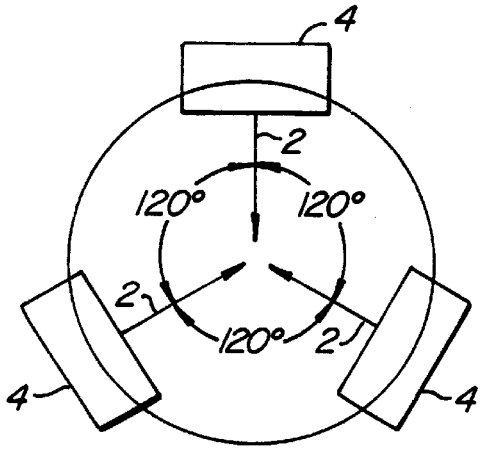
FIG. 1B. PRIOR ART
Figure 1C:
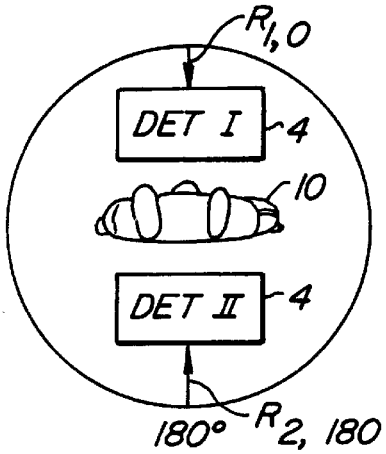
FIG. 1C. PRIOR ART
FIGS. 1C–1E are schematic views showing 3 of the multiple angular stops required for a 360° scan with the angular displacement of the detectors at 180°.
Figure 1D:
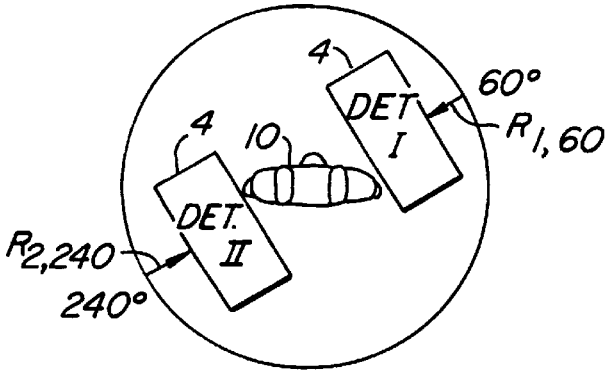
FIG. 1D. PRIOR ART
Figure 1E:
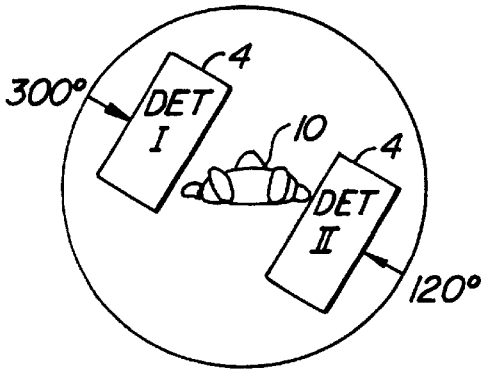
FIG. 1E. PRIOR ART

FIGS. 1C–1E depict the required angular stops for two detectors 4 displaced by 180° to accomplish a 360° scan. In the 180° configuration the size of the detectors does not limit their radial motion and the detectors 4 can be positioned to touch the body 10 of the patient at each stop. However, the detectors cannot be moved in circular path while maintaining close proximity to the body of the patient 10 because the body 10 of the patient is not circular.

Figure 2A:
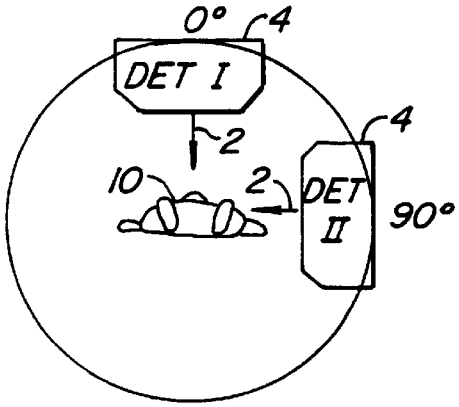
FIGS. 2A–2C are schematic views showing 3 of the multiple angular stops required for a 180° scan with the angular displacement of the detectors at 90°.
Figure 2B:
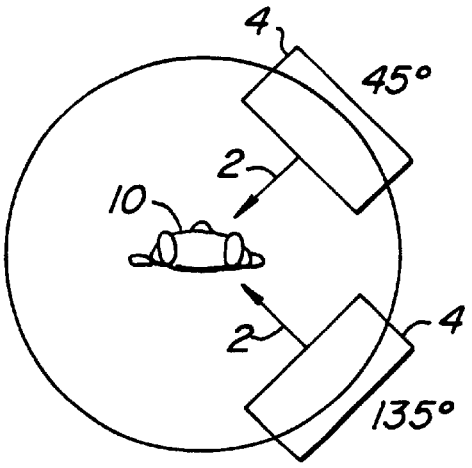
Figure 2C:
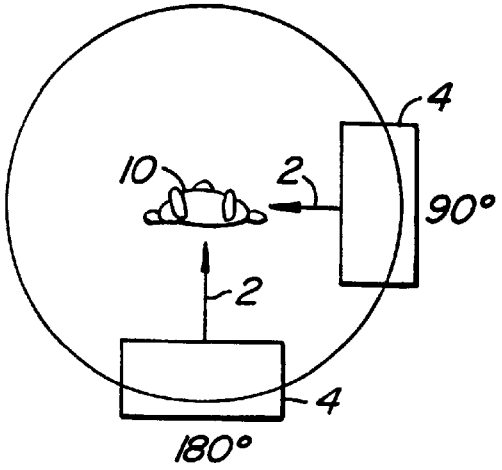

FIGS. 2A–2C depict a preferred embodiment of the invention. The detectors 4 have their image direction arrows oriented at 90° to reduce the imaging time of a 180° scan to ½ the imaging time of a single-head system because data is acquired from two stops simultaneously.

Figure 3:
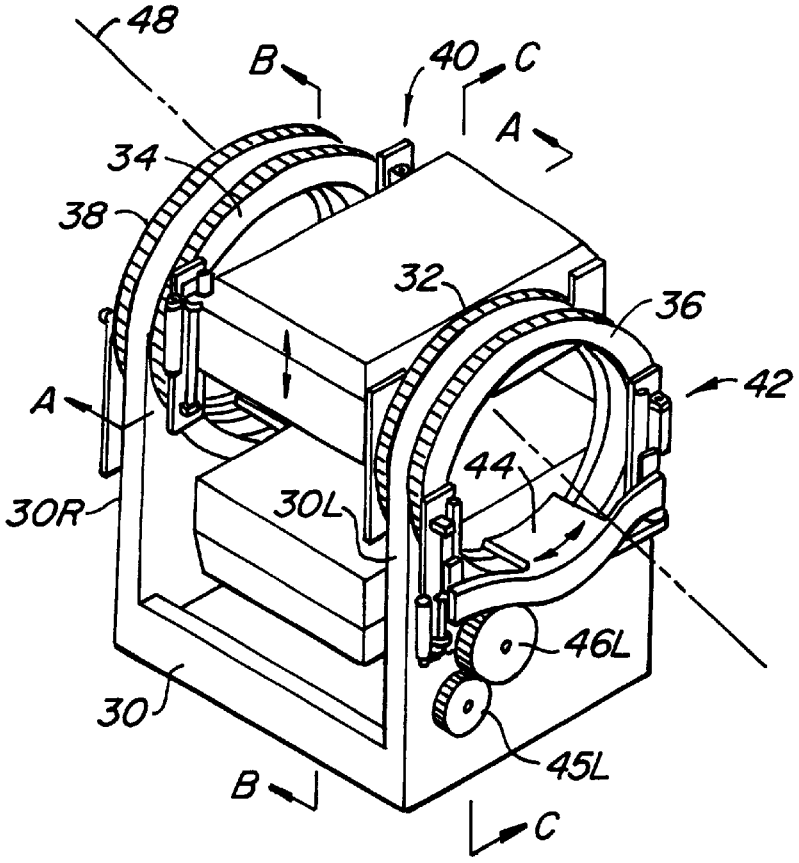
FIG. 3 is a perspective view of a preferred embodiment of the invention.

FIG. 3 is a perspective view of a preferred embodiment of the invention that allows the adjustment of the relative angular displacement of the detectors to have any magnitude from less than 90° up to 180°. Further, each detector may be independently moved toward or away from the lateral axis 48.

In FIG. 3, a gantry 30, having left and right upright sections 30L and 30R, supports first and second detector I drive gear rings 32 and 34 and first and second detector II drive gear rings 36 and 38. A detector I radial motion mechanism 40 connects detector I to the interior surface of the second detector I drive gear ring 34 and a detector II radial motion mechanism 42 connects detector II, via a first detector II support arm 44, to the exterior surface of the first detector II drive gear ring 36.

A left drive gear 45L and idler gear 46L controllably engages the first detector drive gear ring 36 to move detector II in a circular path about a lateral axis 48.

Figure 4:
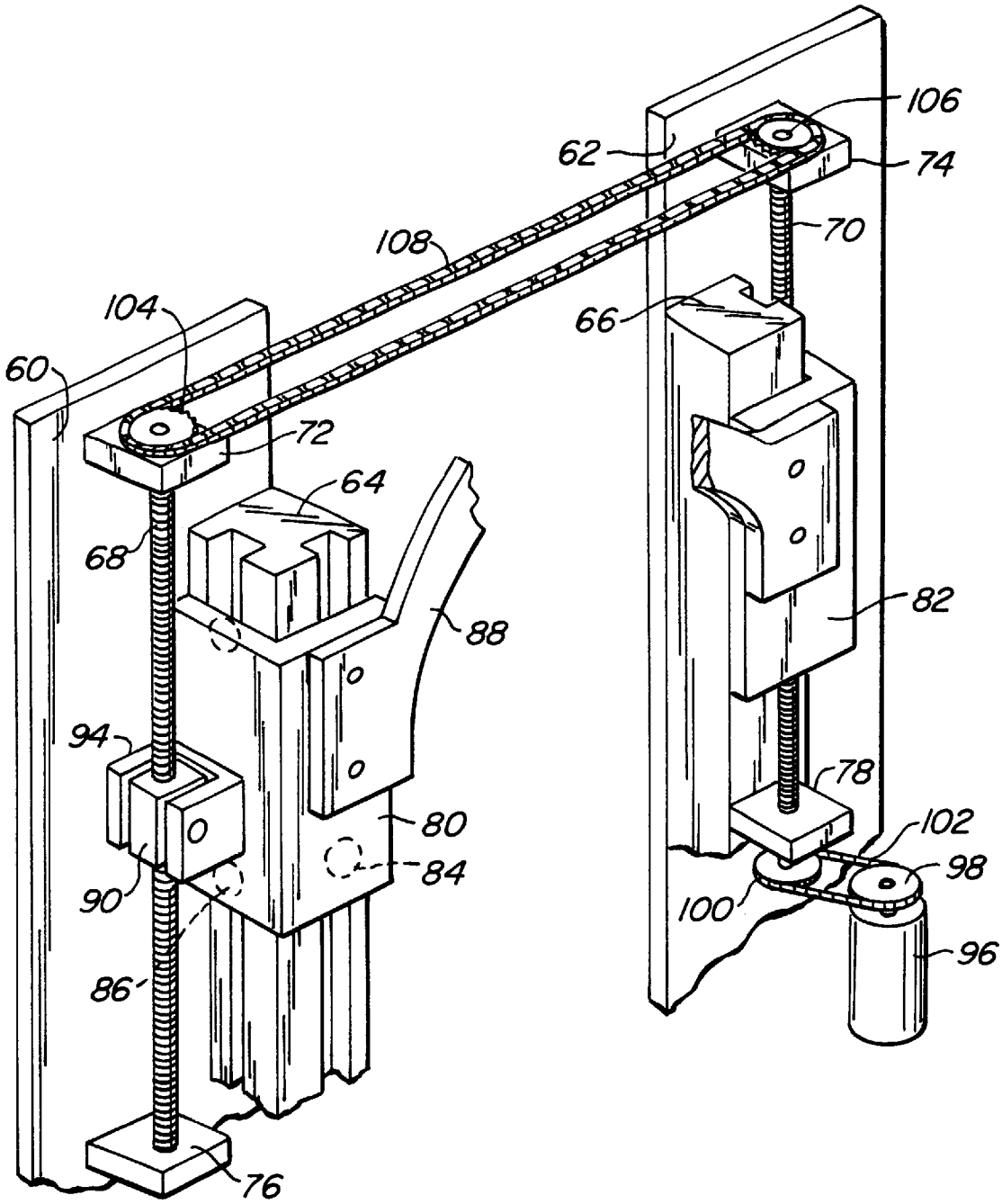
FIG. 4 is a view taken along A—A of FIG. 3.

FIG. 4 is perspective view of the detector I radial motion mechanism 40 taken along A—A of FIG. 3. In FIG. 4, base plates 60 and 62 having slotted guide bars 64 and 66 fixedly mounted thereon, are attached to the interior surface of the second detector I ring gear 34. Lead screws 68 and 70 are rotatably mounted in bearing blocks 72, 74, 76, and 78 which are fixedly attached to the base plates 60 and 62. Arm supports are engaged with the grooves of the guide bars 64 and 66 by guide rollers 84 and 86. Swivel nuts (only one 90 is shown) couple the lead screws to the arm supports 80 and 82 via brackets (only one 94 is shown). A detector support arm 88 is fixedly mounted to the arm supports 80 and 82.

A drive motor has a lead drive gear 98 coupled to a trailer gear 100 mounted on the second lead screw 70 by a drive chain 102. First and second lead screw coupling gears 104 and 106 are coupled by a coupling chain 108.

Figure 5:
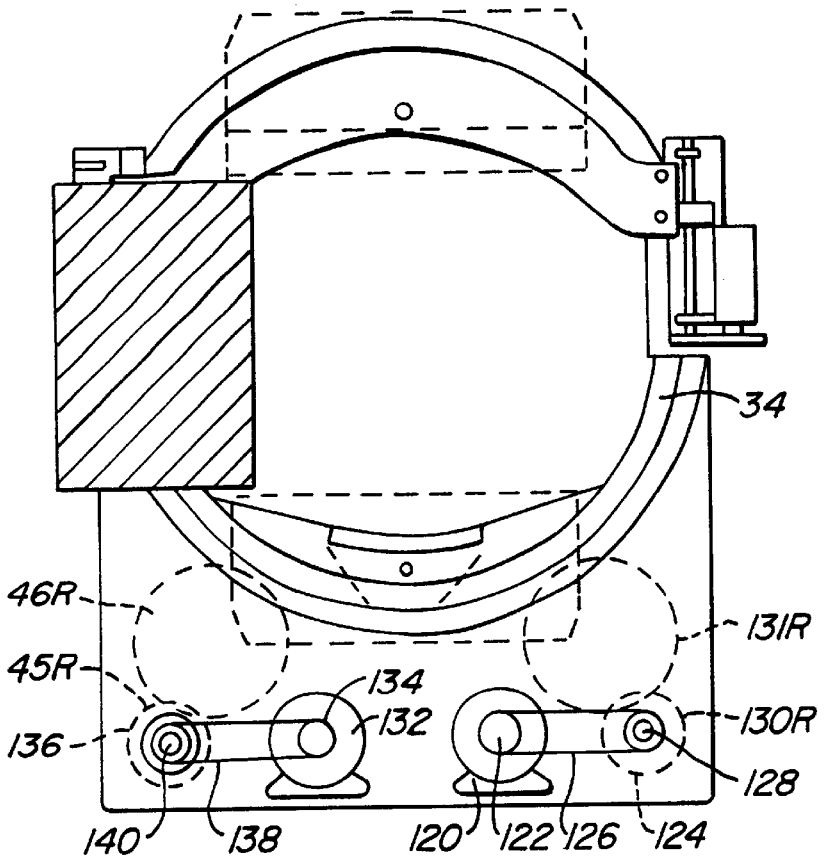
FIG. 5 is a view taken along B—B of FIG. 3.

FIG. 5 is an end view, taken along B—B of FIG. 3, of the rotary drive mechanisms for detectors I and II. In FIG. 5, a first rotary drive motor 120 has a lead drive pulley 122 coupled to a transmission shaft drive pulley 124 by a first drive belt 126. A first transmission shaft 128 is coupled to the second detector I ring gear 34 by a right drive gear 130R and idler gear 131R. The first transmission shaft extends through the gantry 30 parallel to the lateral axis 48 and is also coupled to the first detector I ring gear 32 by left drive and idler gears 130L and 131L (not shown). The drive and idler gears 130 and 131 for driving the detector I ring gears 32 and 34 are located on the interior sides of the upright sections 30L and 30R of the gantry 30.

Similarly, a second rotary drive motor 132 has a lead drive pulley 134 coupled to a transmission shaft drive pulley 136 by a second drive belt 138. A second transmission shaft 140 is coupled to the second detector II ring gear 38 by a right drive gear 45R and idle gear 46R (depicted in phantom). The second transmission shaft extends through the gantry 30 parallel to the lateral axis 48 and is also coupled to the second detector II ring gear 36 by drive and idler gears. The drive and idler gears 45 and 46 for driving the detector II ring gears 36 and 38 are located on the exterior sides of the upright sections 30L and 30R of the gantry 30.

Figure 6:
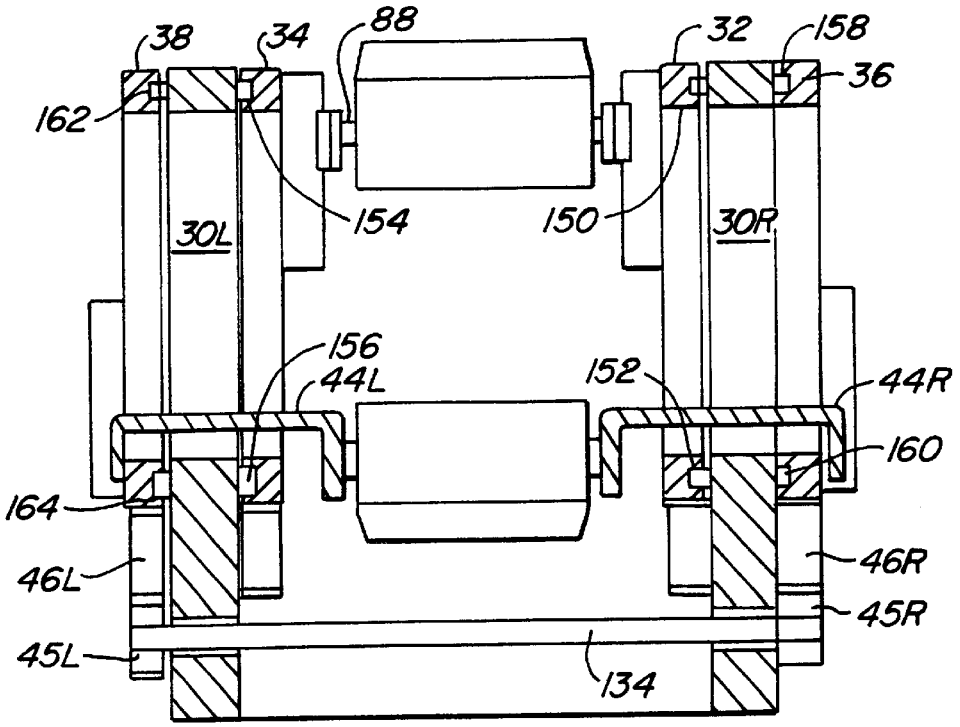
FIG. 6 is a view taken along C—C of FIG. 3.

FIG. 6 is a cross-sectional view, taken along C—C of FIG. 3, depicting the drive and detector support mechanisms. The detector ring gears 32, 34, 36, and 38 have support grooves which are engaged with gear support bearings 150, 152, 154, 156, 158, 160, 162, and 164 mounted on the upright sections 30L and 30R of the gantry 30. Detector I and the detector I radial drive mechanism are mounted on the interior surfaces of the first and second detector I ring gears 32 and 34. The radial drive mechanism for detector II is mounted on the exterior surface of the detector II ring gears 36 and 38. The detector II support arms 44R and L are coupled to the exterior surfaces of the detector II ring gears and extend through the annular space created by the ring gears and supports detector II.

Figure 7:
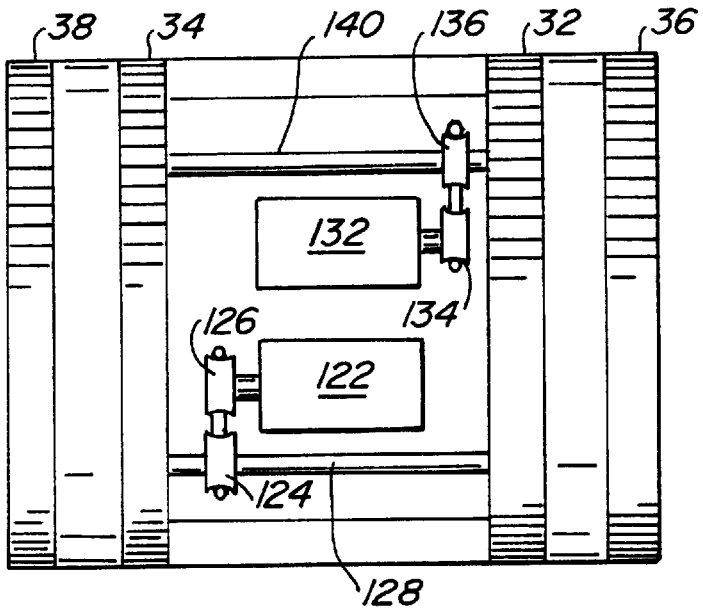
FIG. 7 is a top view of the embodiment depicted in FIG. 3.

FIG. 7 is a top view of the embodiment depicted in FIG. 3 and further depicts the details of the rotary drive mechanism. The first transmission shaft 128 transmits the rotary motion of the first rotary drive motor 122 to both the first and second detector I ring gears 32 and 34 and the second transmission shaft 140 transmits the rotatory motion of the second rotary drive motor 132 to the first and second detector II ring gears 36 and 38.

The operation of the embodiment depicted in FIGS. 3–7 will now be described. Detectors I and II may be independently rotated about the lateral axis 48 by activating either the first or second rotary drive motors 132 or 122. If the first rotary motor is activated rotary motion is transmitted to the first detector ring gears 32 and 34 which in turn impart rotary motion to detector I through the support arms 88.

Additionally, each detector may be independently moved radially toward or away from the lateral axis 48 by activating the radial drive motor 96 in the radial drive mechanism for the detector.

Figure 7A:
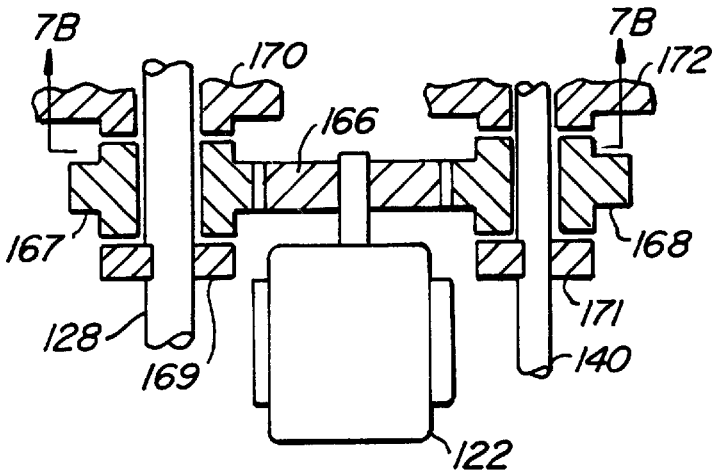
FIGS. 7A–7C are a schematic views of an alternative rotational drive mechanism.
Figure 7B:
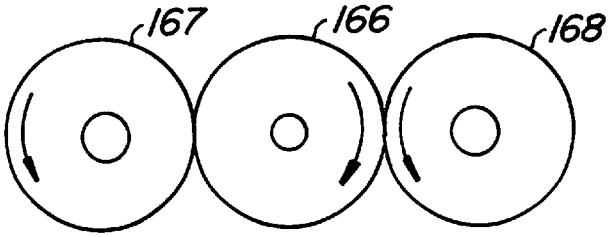

FIGS. 7A and 7B depict an alternative rotary drive mechanism utilizing a single rotary drive motor 122 coupled to the first and second transmission shafts 128 and 140. In FIG. 7A a lead drive gear 166 is directly coupled to the shaft drive gears 167 and 168 to rotate both transmission shafts 128 and 140 in the same direction.

The rotational motion of shaft drive gear 166 is transmitted to the first transmission shaft 128 when a first electromagnetic clutch 169 is engaged and rotation of the first transmission shaft 128 is stopped when a first electromagnetic brake 170 is engaged. Similarly, the rotational motion of shaft drive gear 166 is transmitted to the second transmission shaft 140 when a second electromagnetic clutch 171 is engaged and rotation of the second transmission shaft 140 is stopped when a second electromagnetic brake 172 is engaged.

FIG. 7B is a view, taken along 7B—7B of FIG. 7A, depicting the rotation of the lead gear 166 and shaft drive gears 167 and 168.

In operation, both detectors I and II are rotated when both clutches 169 and 170 are engaged and both brakes 170 and 172 are disengaged. Detector I is moved independently if the first clutch 169 is engaged and the first brake 170 is disengaged and detector II is moved independently if the second clutch 171 is engaged and the second brake 172 is disengaged. The brakes are used for safety reasons and to counteract the system imbalance.

Figure 7C:
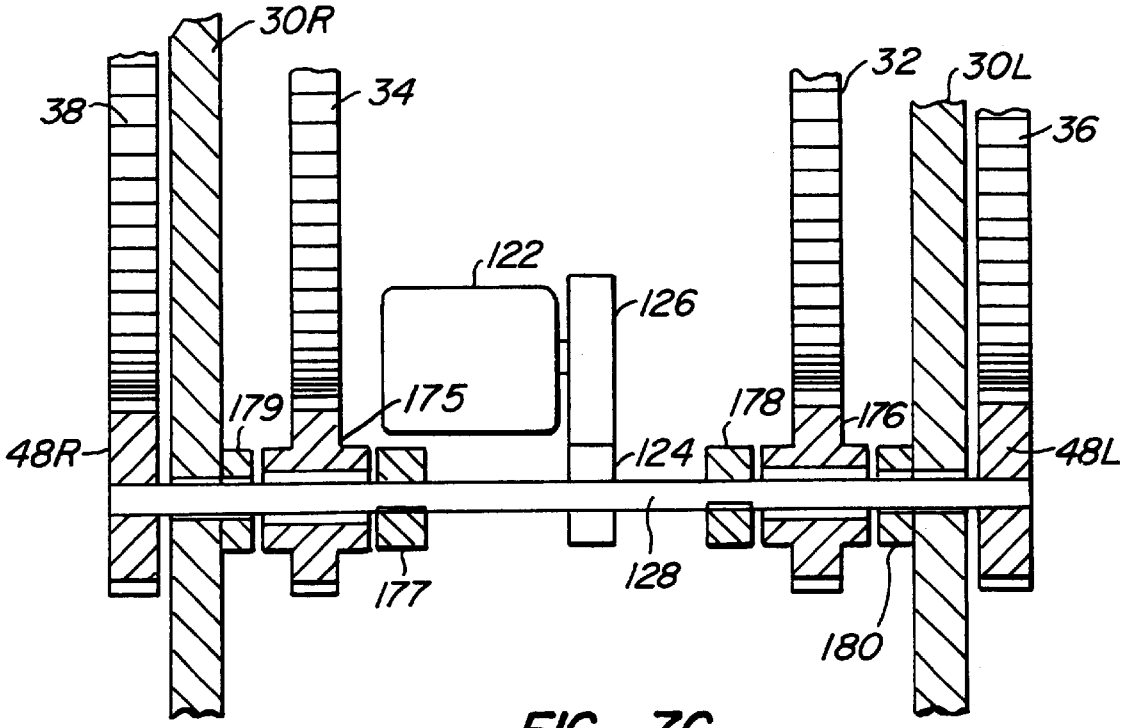

FIG. 7C is a schematic view of an alternative drive system that uses a single drive motor 122 and drive shaft 128. Drive gears 48 are fixed on the end of the shaft 128 and engaged with the first and second detector II ring gears 36 and 38. First and second shaft gears 175 and 176 couple the rotational motion of the shaft 128 to the first and second detector I ring gears 32 and 34 when electromagnetic clutches 177 and 178 are engaged and the motion of the first and second detector I ring gears 32 and 34 is stopped when the electromagnetic brakes 179 and 180 are engaged.

In operation, both detectors rotate together when both clutches 177 and 178 are engaged and the brakes 179 and 180 are released and the rotational drive motor 122 is activated. Detector II is independently rotated to adjust the angular displacement relative to detector I when the brakes 179 and 180 are engaged and the clutches 177 and 178 are released.

Figure 8:
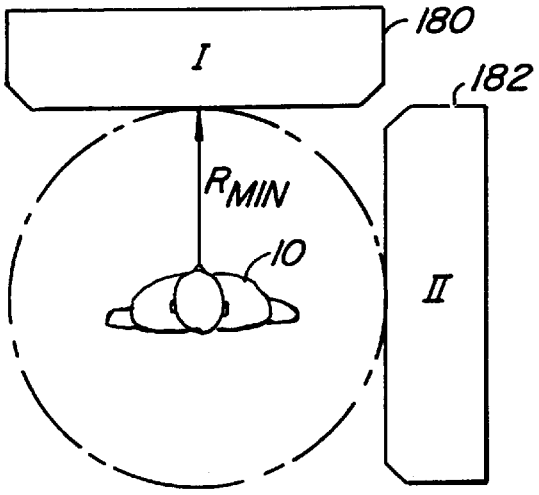
FIG. 8 is a schematic view of two detectors oriented at 90°.

As described above, high patient throughput requires that detectors having a wide field of view be utilized. However, when the detector image direction arrows 2 are oriented at 90°, to efficiently perform a 180° scan, the physical size of the detectors 4 limits their radial motion. Referring to FIG. 8, the detector edges will touch when the radius Rmin is reached. Thus the detectors 4 are not able to touch the body 10 of the patient which is necessary to achieve high resolution. Also, each detector 4 has a lateral shielding section 182 to prevent external gamma rays from reaching the scintillation medium.

Figure 9:
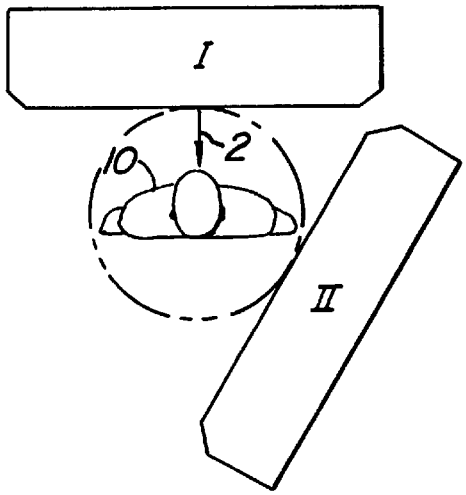
FIG. 9 is a schematic view of two detectors oriented at 120°.

In one embodiment of the invention the detector image direction arrows 2 are oriented at 120° when a 180° scan is to be performed. As depicted in FIG. 9, this orientation allows greater radial motion to allow the detectors 4 to be positioned closer to the body 10 of the patient than in the 90° configuration. However, the imaging time is reduced to only about ⅔ of the imaging time of a single-head system because both detectors 4 are within the 180° arc only a fraction of the time.

Figure 10:
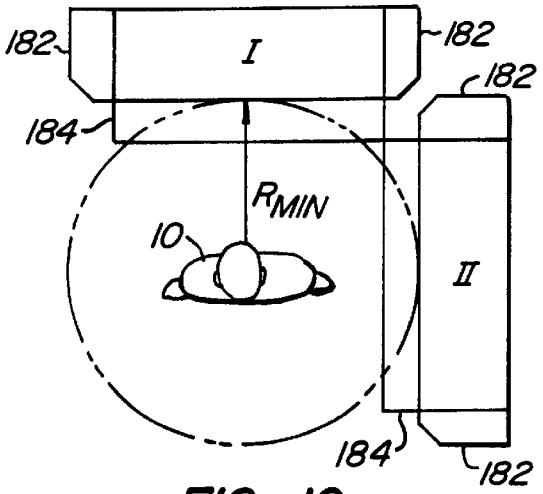
FIG. 10 is a schematic view of two detectors having extended collimators and oriented at 90°.

In another embodiment, depicted in FIG. 10, extended collimators 184 are utilized to decrease Rmin and to place the collimator 184 closer to the body 10 of the patient.

Figure 10A:
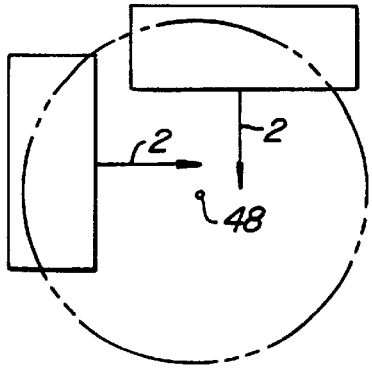
FIG. 10A is a schematic view of two detectors having their centers displaced from the lateral axis.

In FIG. 10A, a configuration where the centers of the detectors 4 are displaced from the lateral axis 48 so that the image arrows 2 do not point toward the lateral axis is depicted. SPECT algorithms for correcting for such displacements are known in the art.

Figure 11:
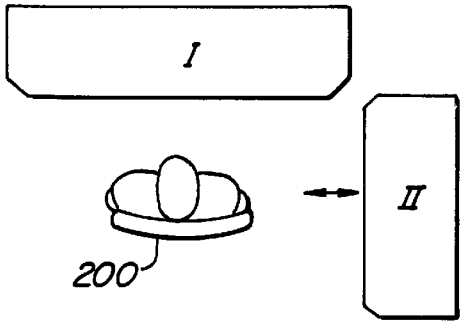
FIG. 11 is a schematic view of two detectors oriented at 90° with a reduced lateral detector.

Alternatively, as depicted in FIG. 11, detector II is oriented laterally to the body 10 of the patient and has a narrower cross-section and field of view. The smaller cross-section of detector II facilitates closer positioning of the collimator to the body of the patient.

Figure 12:
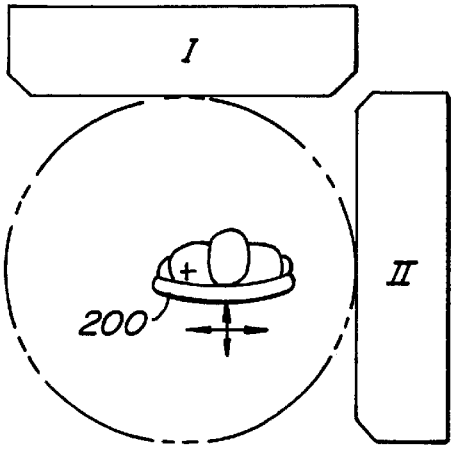
FIG. 12 is a schematic view depicting a patient table that can be horizontally and vertically displaced relative to the lateral axis.

In another embodiment of the invention, depicted in FIG. 12, a table 200 holding the patient is displaced vertically and horizontally from the lateral axis 48 so that the body 10 of the patient touches the detectors 4.

Figure 13A:
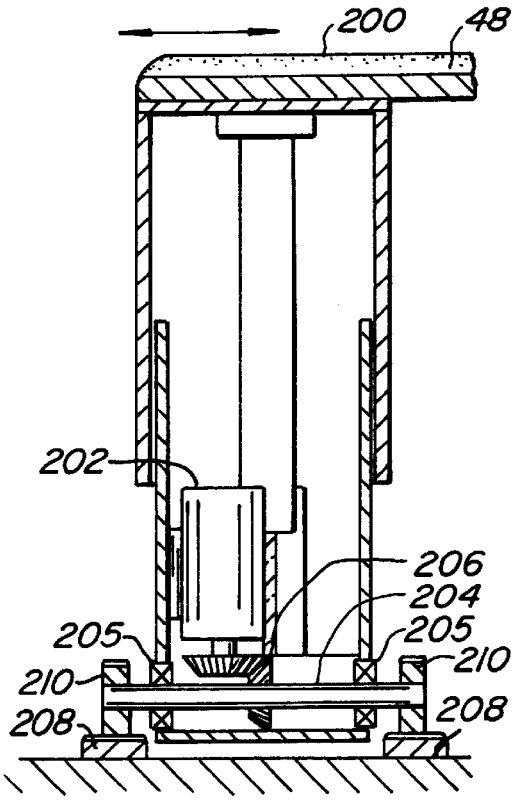
FIGS. 13A and 13B are cut away views of mechanisms for displacing the table from the lateral axis.

FIGS. 13A and B depict mechanisms for imparting horizontal motion and vertical motion of the table 200 relative to the lateral axis 48. In FIG. 13A, a view taken perpendicular to the lateral axis 48, a horizontal drive motor 202 imparts rotary motion to an axle 204, supported by bearings 205, through bevel gear 206. Horizontal motion of the table 200 is effected by movement along gear racks 208, oriented parallel to the lateral axis 48, through rotational motion imparted to gears 210 engaged to gear racks 208 by axle 204.

Figure 13B:
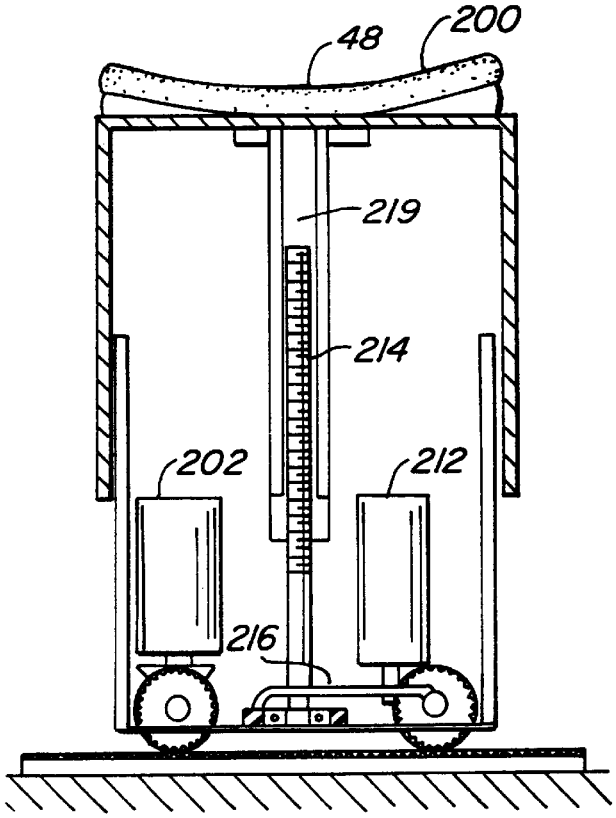

In FIG. 13b, a view taken perpendicular to the lateral axis 48, a vertical drive motor 212 imparts rotational motion to a lead screw 214 through a drive mechanism 216. The threads of the lead screw 214 are engaged to threads of a telescope tube 219 to impart vertical motion to the telescope tube and table 200 when the vertical drive motor 212 is activated.

Figure 14:
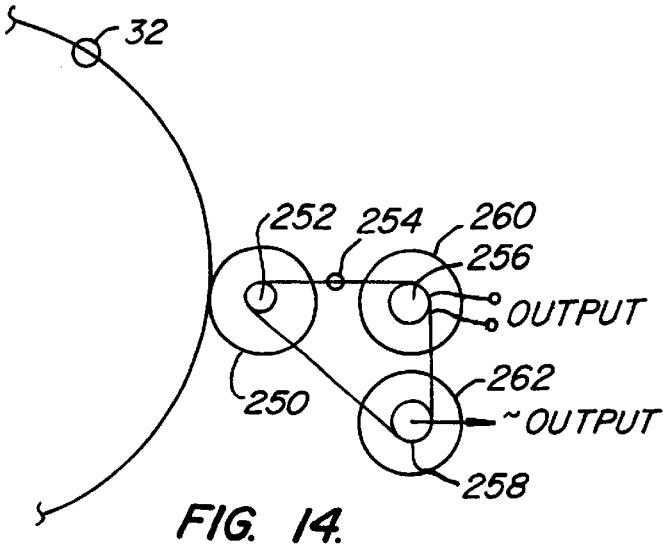
FIG. 14 is a schematic view of a positional feedback mechanism.

FIG. 14 depicts a positional feedback device for indicating the positions of the detectors. In FIG. 14, a sensor gear 250 engages a ring gear 32 and has a sprocket 252 coupled to a chain 254. The chain engages sprockets 256 and 258 coupled to a potentiometer 260 and an encoder 262.

In operation, the potentiometer 260 is used for coarsely indicating position and the encoder 262 for finely indicating position. For example, the sprockets can be sized so that for each revolution of the ring gear 32 the potentiometer 260 makes 10 turns varying the resistance from 0 to 1,000 ohms. If power is lost the potentiometer 260 will not loose its position or reading.

Similar devices are utilized to indicate the radial position of the detectors and the vertical and horizontal displacement of the table 200.

Figure 15A:
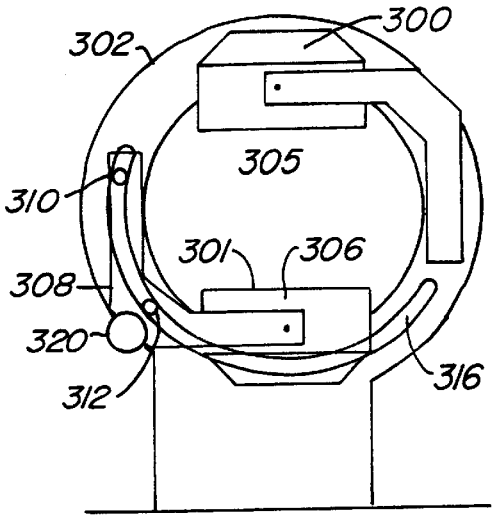
FIGS. 15A and 15B are schematic views of an alternative means for varying the angular displacement between the detectors.
Figure 15B:
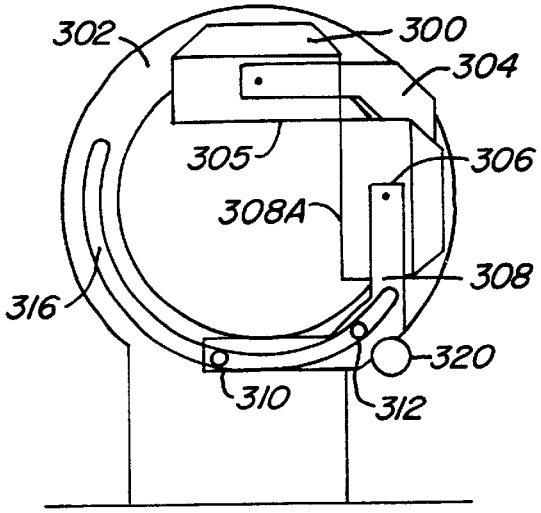

FIGS. 15A and 15B depict an alternative mechanism for adjusting the angular displacement between the detectors between 90° and 180°. FIG. 15A depicts the detectors positioned 180° apart. FIG. 15B depicts the detectors positioned 90° apart. Detector I 300 is fixedly attached to ring gear 302 through cantilever support arm 304. Detector II 306 is attached to ring gear 302 through cantilever support arm 308. The angular displacement between the detectors is varied by moving detector II 306 in a circular path along the ring gear 302.

Figure 16:
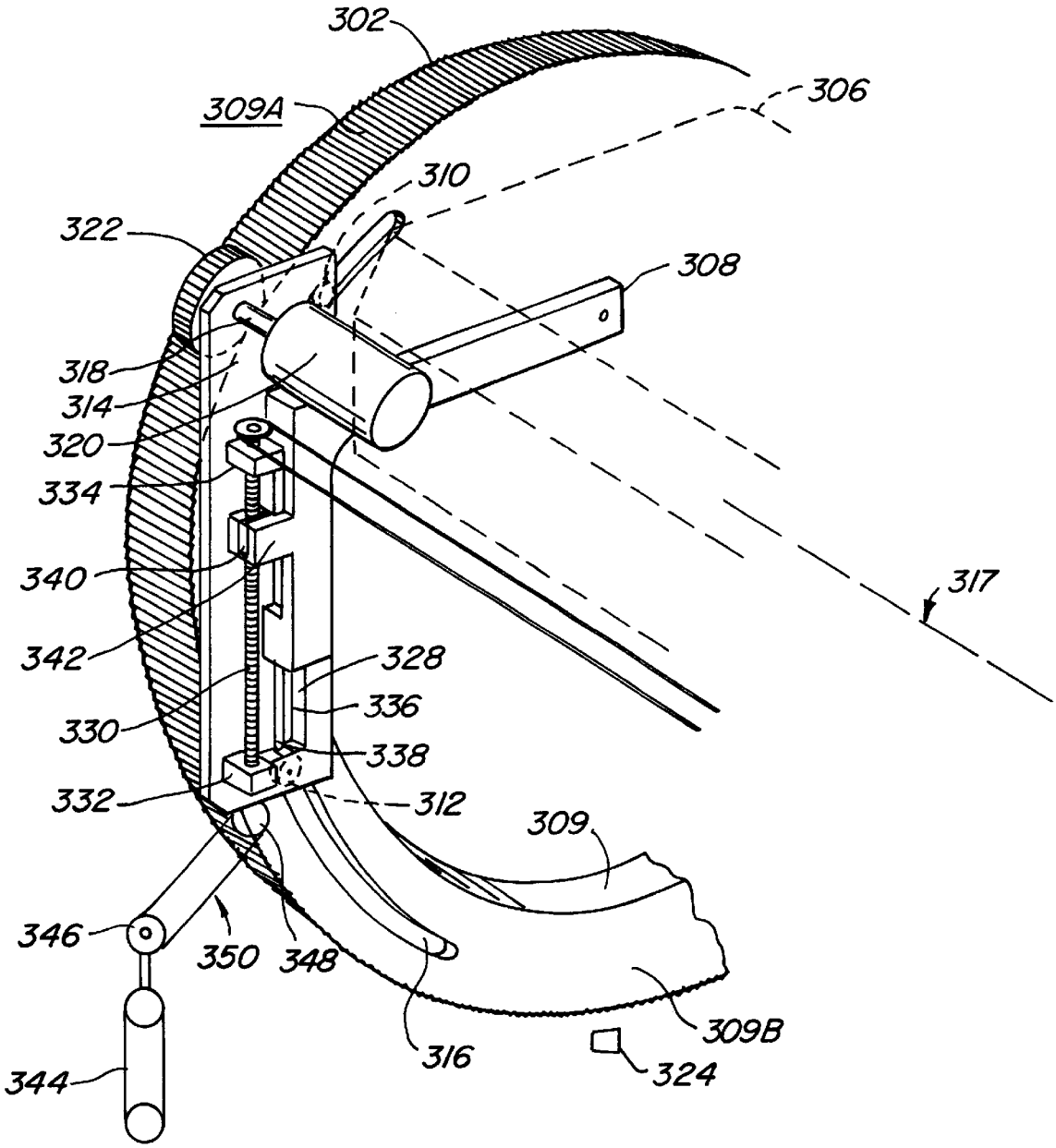
FIG. 16 is a perspective view of an alternative means for varying the angular displacement between the detectors.

FIG. 16 shows the coupling of detector II 306 to ring gear 302 in greater detail. Guide rollers 310 and 312 are rotatably mounted to baseplate 314. These guide rollers engage a groove 316 along an arc parallel to the circumference of the ring gear 302 and on the ring gear's interior surface. Transmission shaft 318 is rotatably mounted to baseplate 314 and is driven by motor 320. This transmission shaft is fixedly attached to angular displacement gear 322 which is engaged to ring gear 302. A brake 324 is coupled to ring gear 302. In an alternative embodiment the brake 324 is coupled to ring gear 302 through a shaft which drives the ring gear through a drive gear.

The operation of the embodiment depicted in FIGS. 15A, 15B and 16 will now be described. Rotating ring gear 302 with brake 324 disengaged causes both detectors I and II 300 and 306 to move in a circular path around the lateral axis 326. Rotating angular displacement gear 322 through the action of motor 320 with brake 324 engaged causes detector II 306 to move in a circular path around the lateral axis 326 while detector I 300 remains fixed thus varying the angular displacement between detectors I and II 300 and 302.

FIG. 15 depicts part of the radial motion mechanism provided in one embodiment for detector II 306. Base plate 314 having slotted guide bar 328 fixedly mounted thereon, is attached to the interior surface of the ring gear 302. Lead screw 330 is rotatably mounted in bearing blocks 332 and 334 which are fixedly attached to the base plate 314. Detector cantilever support 308 is engaged with the grooves 336 and 338 of the guide bar 328 by guide rollers (not shown). Swivel nut 340 couples the lead screw 330 to the cantilever support 308 via bracket 342. A drive motor 344 has a lead drive gear 346 coupled to a trailer gear 348 mounted on the lead screw by a drive chain 350. Through the operation of this radial motion mechanism, detector II 306 may be moved toward and away from the lateral axis. In one embodiment, a similar radial motion mechanism is provided for detector I 300.

In another embodiment there is a second ring gear parallel to the first ring gear. Both detectors then lie between said rings. One or both detectors are further supported by cantilever supports attached to the second ring gear. In a further embodiment one or both of these cantilever supports are attached to the second ring gear through radial motion mechanisms similar to those described above. Where two radial motion mechanisms support one detector, the coupling gears of the mechanisms are coupled with a coupling chain to allow tandem operation.

Figure 17:
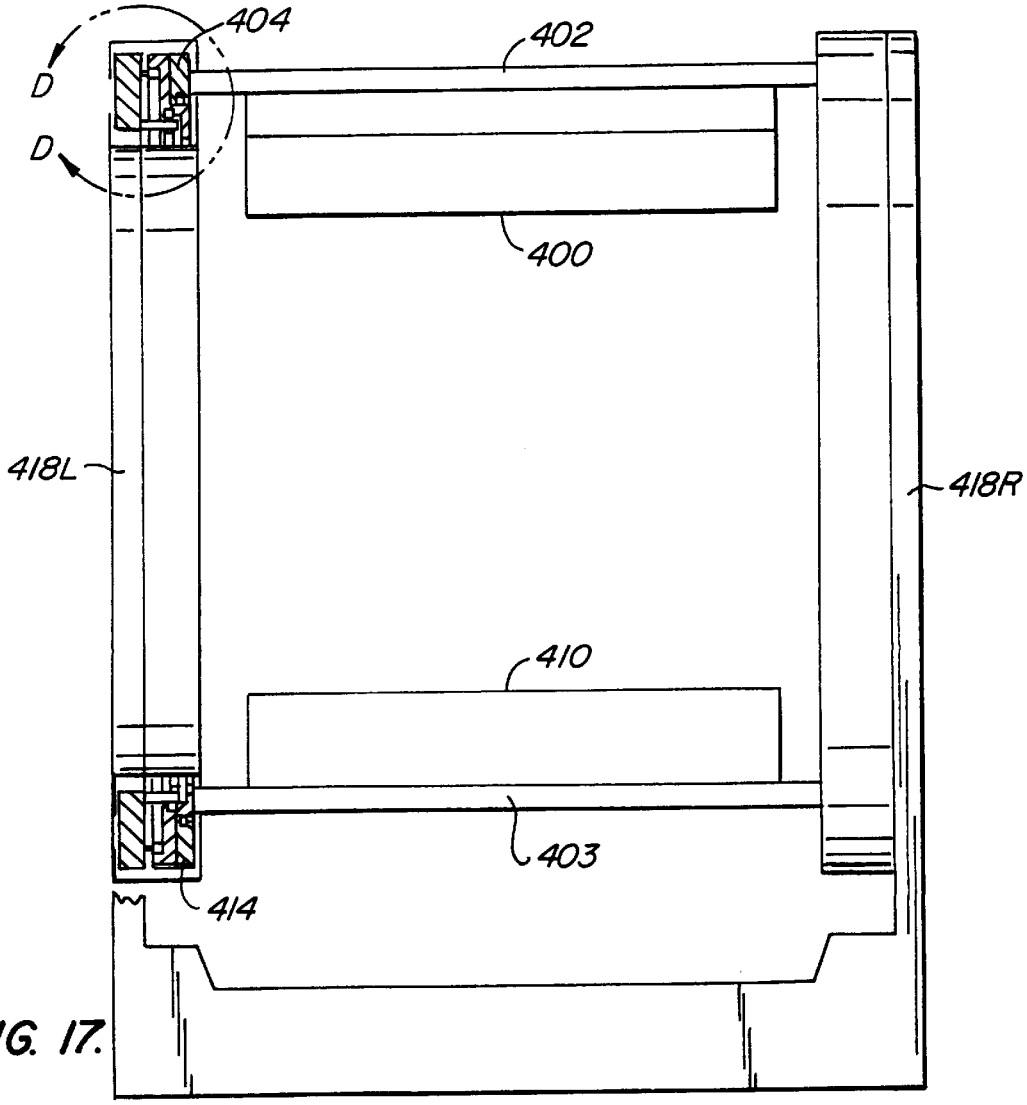
FIG. 17 is a schematic view of an alternative embodiment of the invention showing the positional relationship between the two pairs of ring gears.
Figure 18:
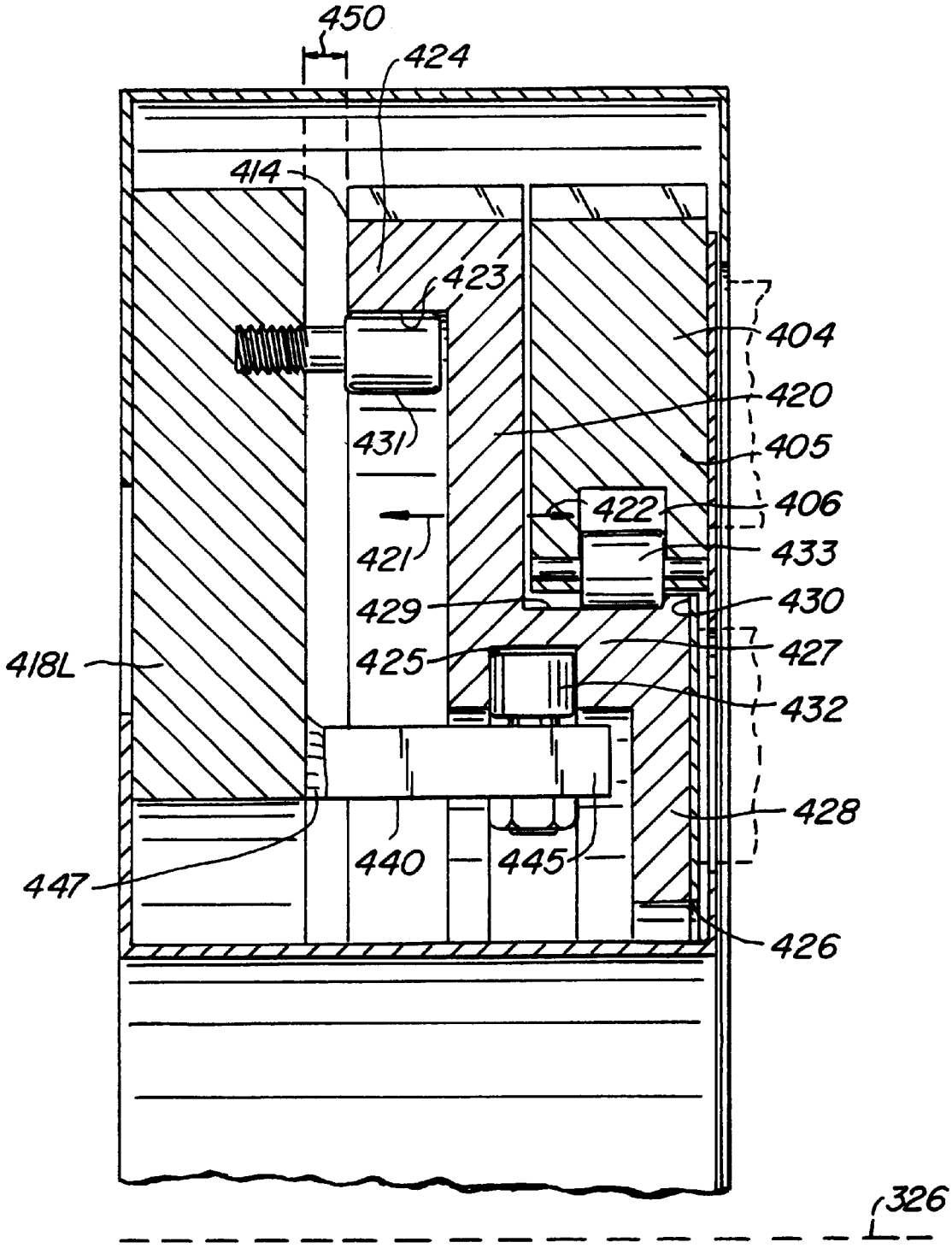
FIG. 18 is a view taken along line D—D of FIG. 17.

FIGS. 17 and 18 depict an alternative mechanism for adjusting the relative angular displacement of the detectors between 90° and 180°. In FIG. 17, Detector I 400 is fixedly attached to a pair of slave gear rings 404 (only one of which is shown) through cantilever support arm 402. Detector II 410 is attached to a pair of master gear rings 414 (only one of which is shown) through cantilever support arm 403. The angular displacement between Detector I 400 and Detector II 410, which is 180 degrees in FIGS. 17 and 18, is varied by independently rotating slave gear rings 404 in relation to master gear rings 414 via the operation of drive assembly 500 (See FIG. 19) as will be described in more detail hereinafter.

FIG. 18 shows the coupling of one of the slave gear rings 404 to a respective master gear ring 414 proximate gantry wall 418L in greater detail. It is to be understood that the coupling of the other slave gear ring 404 to its respective master gear ring 414 proximate gantry wall 418R is accomplished in a similar manner to the coupling of the gear rings proximate wall 418L, the former merely being a mirror image of the latter. Master gear ring 414 is located between the gantry walls 418L and 418R and is oriented substantially perpendicular to and approximately centered on the lateral axis 326. Master gear ring 414 includes a main cylindrical body 420 which has an inner face 422 and an outer face 421. Outer radial flange 424 is integral with and perpendicular to the upper region of the outer face 421 and is located adjacent gantry wall 418L. The outer flange 424 defines a radial abutment undersurface 423 for engaging guide rollers 431, which are rotatably fixed within and radially spaced-apart around the entire inner peripheral surface of gantry wall 418L. In the preferred embodiment of the invention, there are ten guide rollers 431 secured to gantry wall 418L which are positioned to engage and rotate along abutment surface 423. This helps to securely position the master gear ring 414 adjacent the gantry wall 418L (and 418R).

Master gear ring 414 also includes an L-shaped inner flange 426 having first and second members 427, 428. First member 427 is integral with and perpendicular to a middle portion of the inner face 422 and defines an upper radial support surface 429 for engaging guide rollers 433 rotatably fixed to slave gear ring 404, as will be described in more detail hereinafter. The second member 428 of the L-shaped flange 426 is integral with and perpendicular to first member 427 and is disposed towards the lateral axis. Second member 428 has an integral upper lip 430 which extends above radial support surface 429 and prevents slave gear ring 404 from falling off of support surface 429. The second member 428 of the L-shaped inner flange and the lower portion of the inner face 422 of the cylindrical body 420 define between them an inner radial groove 425.

Slave gear ring 404, which is positioned about radial support surface 429, has radially spaced apart guide rollers 433 rotatably attached to an inner radial groove 406 formed in side wall 405 of the slave gear ring. The preferred embodiment of the invention is provided with twelve guide rollers 433 equidistantly positioned along the entire inner periphery of radial groove 406 which are secured in place by upper lip 430 and which are free to rotate along radial support surface 429 as will be described in more detail hereinafter. FIG. 18 also shows one of several adjustment blocks 440 that is used to vary the lateral displacement 450 between master gear ring 414 and gantry wall 418L. Each adjustment block 440 includes a guide roller 432 which is rotatably attached at the distal end 445 of adjustment block 440 and is positioned within inner radial groove 425 formed in master gear ring 414. In the preferred embodiment of the invention, there are six adjustment blocks 440 and six corresponding guide rollers 432 radially spaced apart along the entire circumference of the inner surface of gantry wall 418L. Guide rollers 432 are used to secure the gear rings 414, 404 proximate the gantry wall while also being free to rotate within inner radial groove 425 in master gear ring 414. Adjustment block 440 also includes a pair of guide slots (not shown) at its proximal end 447 which are used to change the axial position of adjustment block 440 within gantry wall 418L to thus allow for variations in the lateral displacement of master gear ring 414 relative to the gantry wall 418L.

Figure 19:
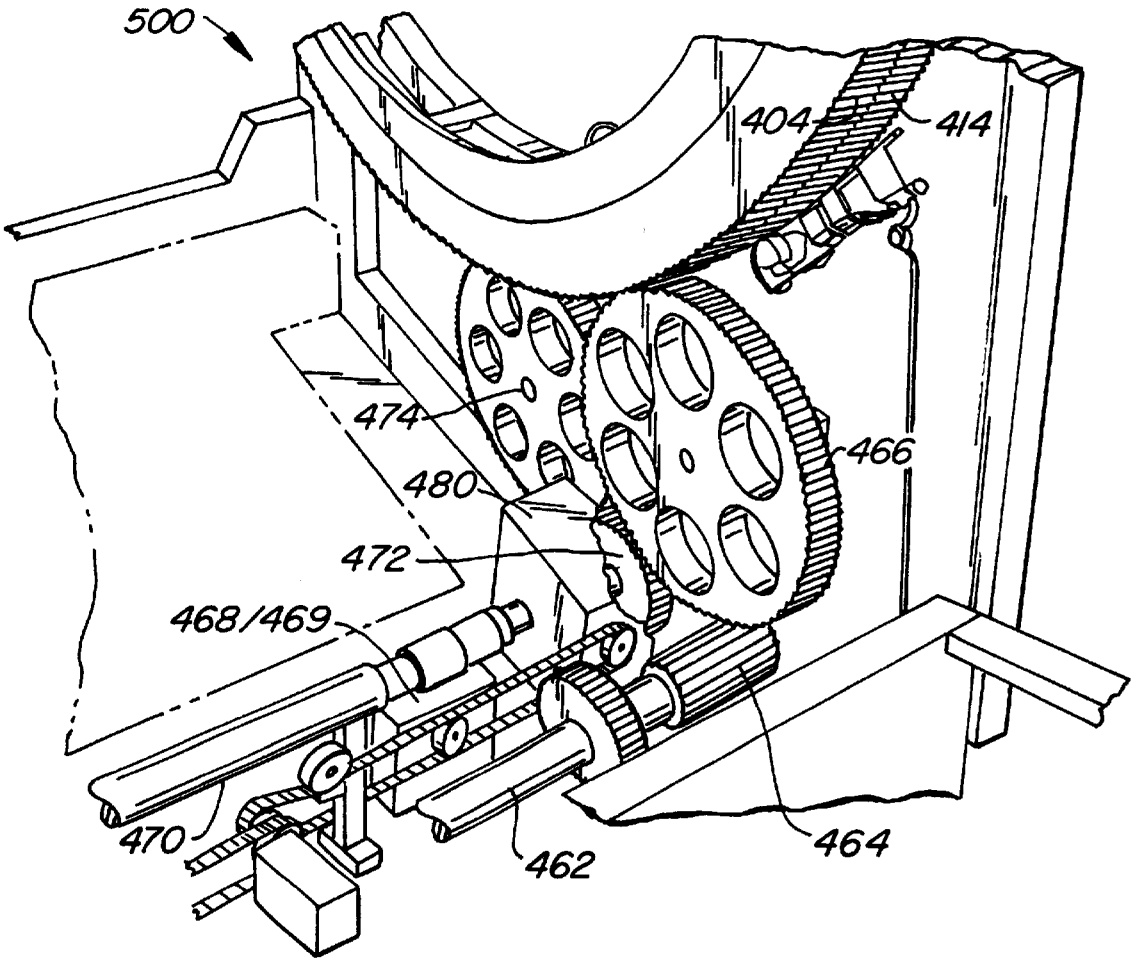
FIG. 19 is a perspective view of the rotational drive assembly for the alternative embodiment of FIG. 17.
Figure 20:
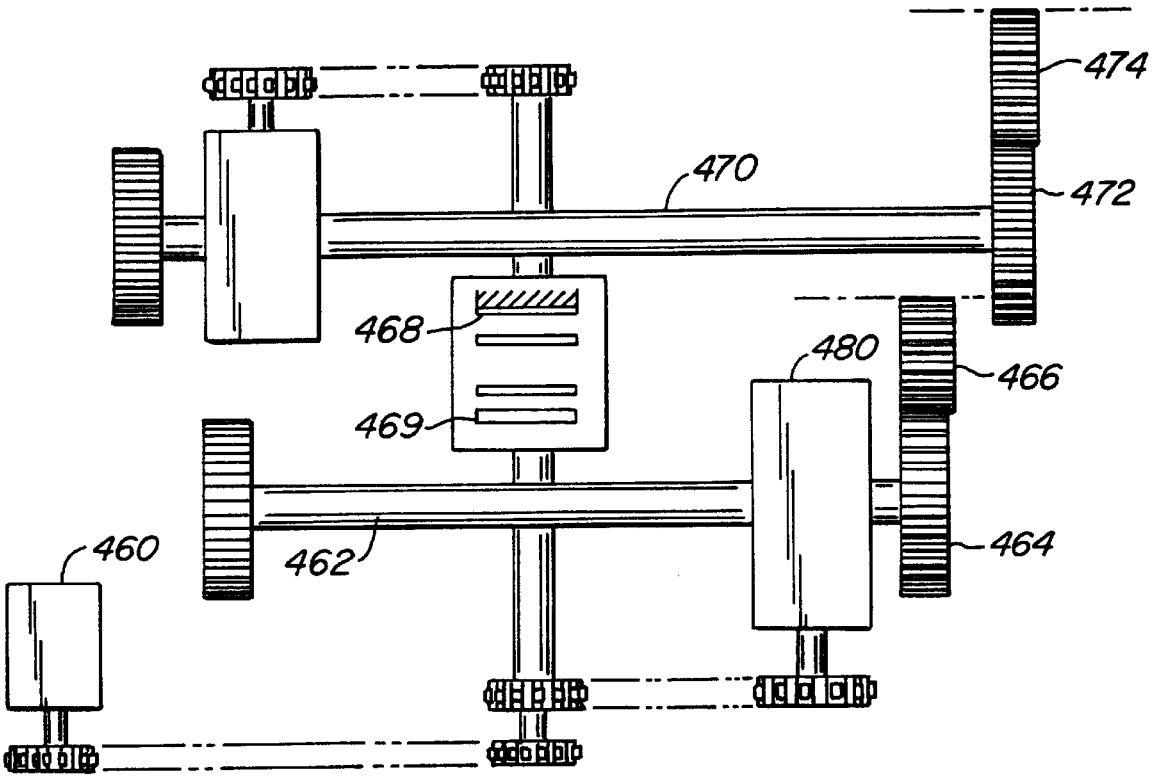
FIG. 20 is a schematic elevational view of the rotational drive assembly of FIG. 19.

FIGS. 19 and 20 depict the embodiment of the drive assembly 500 that is used to rotate master gear rings 414 and slave gear rings 404. Drive assembly 500 includes single motor 460 that is operatively coupled to drive shafts 462 and 470. A pair of drive gears 464 is rigidly attached to drive shaft 462 at opposite ends of the shaft and is in engaging contact with a pair of idler gears 466. Each one of the idler gears 466 engages a respective one of the slave gear rings 404. A pair of drive gears 472 are similarly rigidly attached to drive shaft 470 at opposite ends of the shaft and are in engaging contact with idler gears 474. Each one of the idler gears 474 engages a respective one of the master gear rings 414. A 90 degree gear drive 480 is also coupled to each drive shaft 462 and 470 and is used to help reduce back-driving of the respective drive gears 464 and 472. Drive assembly 500 also includes brake 468 coupled to clutch 469 which function together to inhibit rotation of drive shaft 470 and thus allow slave gear rings 404 to rotate independently of master gear rings 414 as will now be described with reference to FIGS. 17, 18, and 19.

With brake 468 disengaged and clutch 469 engaged, the operation of motor 460 results in the rotation of both of the drive shafts 462, 470 which causes all of the drive gears 464, 472 attached to the shafts to rotate simultaneously. This forces idler gears 466, 474 to rotate which in turn rotates slave gear rings 404 and master gear rings 414 in tandem. As best seen in FIG. 18, each slave gear ring 404 rotates around radial support surface 429 of each respective master gear ring 414 through the rotation of guide rollers 433, which effectively act like bearings. Each master gear ring 414 likewise rotates about guide rollers 431 and 432, in tandem with the rotation of slave gear ring 404. Such an operation allows Detector I 400 and Detector II 410 to rotate together with a fixed angular displacement between them.

When brake 468 is engaged and clutch 469 is disengaged, brake 468 engages drive shaft 470 to prevent its movement. Operation of motor 460 thereby causes only the rotation of drive shaft 462 and gears 464, 466 attached thereto, while gears 472 and 474 remain in a fixed position. As a result, slave gear rings 404 rotate independently of master gear rings 414. As each slave gear ring 404 rotates, guide rollers 433 attached thereto are forced to rotate about radial support surface 429 on each respective master gear ring 414 which allows slave gear ring 404 to rotate relative to its respective master gear ring 414. This causes detector I 400 to move in a circular path around the lateral axis 326 while detector II 410 remains fixed thus varying the relative angular displacement of detectors I and II, 400 and 410.

An improved method for imaging that utilizes the movable table 200 will now be described. The table is moved up and down or left and right using microprocessor control and the positional feedback device enables the microprocessor to calculate the position of the table.

First, the motion limits of the detectors and table are defined. The operator moves the detectors to have the desired relative angular displacement (e.g., 90°). The table holding the patient is positioned parallel to the lateral axis. The operator then moves the detectors into the desired position relative to the patient (e.g. anterior and lateral). The operator then moves the table so that the body of the patient touches the lateral detector and the microprocessor stores the x-location. The operator then moves the table so that the body of the patient touches the anterior detector and the microprocessor stores the y-location. The microprocessor then calculates the required table motion based on the size of the detectors, the number of angular stops required, and x and y locations determined above.

Once the motion limits are defined image data is acquired. The table is moved to a location to allow motion of the detectors and the detectors are moved to the first angular stop. The table is then moved to the starting position for the first angular stop and data is acquired. The positions of the detectors are stored. The procedure is repeated until data is acquired for all the required angular stops. The stored location data is utilized to generate an image from the acquired data.

The invention has now been described with reference to the preferred embodiments. Alternatives and substitutions will now be apparent to persons of ordinary skill in the art. For example, if detectors I and II were to be maintained at a fixed angle, e.g., 120° or 90°, then both detectors and their radial drive mechanisms could be attached to the detector I ring gears 32 and 34. Accordingly, it is not intended to limit the invention except as provided by the appended claims.

What is claimed is:

[1. An imaging system for acquiring imaging data generated by an object positioned about a lateral axis to form a SPECT image, said system comprising:

first and second gamma ray detectors;

a first pair of rings, oriented substantially perpendicular to and approximately centered on the lateral axis;

means for coupling said first detector to said first pair of rings, with the first detector pointed toward the lateral axis and disposed between said rings;

an arc shaped groove in each of said first pair of rings being substantially parallel to a circumference of the rings;

means for coupling said second detector to said arc shaped groove; and means for moving said second detector along said arc shaped groove to vary the angular displacement, relative to the lateral axis, between said first and second detectors to predetermined magnitude.]

[2. An imaging system for acquiring imaging data generated by an object positioned about a lateral axis, said system comprising:

first and second detectors each having a collimator surface oriented perpendicularly to the direction said detectors are pointing;

a first ring oriented substantially perpendicular to and approximately centered on the lateral axis;

a first cantilever support coupled to said ring having said first detector mounted thereon;

an arc shaped groove on said ring said groove being substantially parallel to the circumference of said ring;

a second cantilever support having said second detector mounted thereon;

one or more guide rollers rotatably attached to said second cantilever support and engaged to said groove;

a shaft rotatably attached to said second cantilever support;

a gear fixedly attached to said shaft and engaged to said ring;

a motor controllingly coupled to said shaft, whereby the operation of said motor by moving said second cantilever support along said groove varies the orientation, relative to the lateral axis and in said plane, of the collimator surfaces of said first and second detectors between a first position where said collimator surfaces are parallel and a second position where said collimator surfaces are perpendicular.]

[3. The system of claim 2 further comprising:

a radial motion mechanism coupling said first cantilever support to said first ring said radial motion mechanism comprising a first base plate attached to said first ring;

a first slotted guide bar fixedly attached to said first base plate;

one or more guide rollers rotatably attached to said first cantilever support and engaged to said first slotted guide bar;

a swivel nut attached to said first cantilever support through a bracket;

a first lead screw rotatably coupled to said swivel nut, said first lead screw rotatably mounted in a plurality of bearing blocks, said bearing blocks fixedly attached to said first base plate;

a trailer gear fixedly attached to said first lead screw;

a coupling gear fixedly attached to said first lead screw;

a lead drive gear controllingly coupled to said trailer gear through a coupling chain;

a drive motor controlling by coupled to said lead drive gear;

whereby through the action of said drive motor said first detector may be moved toward and away from the lateral axes.]

[4. The system of claim 3 further comprising:

a second ring substantially parallel to said first ring with said detectors lying between said rings;

a third cantilever support coupling said first detector to said second ring;

a second radial motion mechanism coupling said third cantilever support to said second ring, said second radial motion mechanism comprising a second base plate fixedly attached to said second ring;

a second slotted guide bar fixedly attached to said second base plate;

one or more guide rollers rotatably attached to said third cantilever support and engaged to said second slotted guide bar;

a swivel nut fixedly attached to said first cantilever support;

a second lead screw rotatably coupled to said swivel nut, said second lead screw rotatably mounted in a plurality of bearing blocks, said bearing blocks fixedly attached to said second base plate;

a coupling gear fixedly attached to said second lead screw;

a coupling chain coupling said coupling gear of said first radial motion mechanism and said coupling gear of said second radial motion mechanism;

whereby said first radial motion mechanism and said second radial motion mechanism may be operated in tandem to move said first detector toward and away from the lateral axis.]

[5. The system of claim 2 further comprising a radial motion mechanism coupling said second cantilever support to said first ring said radial motion mechanism comprising a first base plate attached to said first ring;

a first slotted guide bar fixedly attached to said first base plate;

one or more guide rollers rotatably attached to said second cantilever support and engaged to said first slotted guide bar;

a swivel nut attached to said first cantilever support through a bracket;

a first lead screw rotatably coupled to said swivel nut, said first lead screw rotatably mounted in a plurality of bearing blocks, said bearing blocks fixedly attached to said first base plate;

a trailer gear fixedly attached to said first lead screw;

a coupling gear fixedly attached to said first lead screw;

a lead drive gear controllingly coupled to said trailer gear through a coupling chain;

a drive motor controlling by coupled to said lead drive gear;

whereby through the action of said drive motor said second detector may be moved toward and away from the lateral axis.]

[6. The system of claim 5 further comprising:

a second ring substantially parallel to said first ring with said detectors lying between said rings;

a third cantilever support coupling said second detector to said second ring;

a second radial motion mechanism coupling said third cantilever support to said second ring said radial motion mechanism comprising a second base plate fixedly attached to said second ring;

a second slotted guide bar fixedly attached to said second base plate;

one or more guide rollers rotatably attached to said third cantilever support and engaged to said second slotted guide bar;

a swivel nut fixedly attached to said first cantilever support;

a second lead screw rotatably coupled to said swivel nut, said second lead screw rotatably mounted in a plurality of bearing blocks, said bearing blocks fixedly attached to said second base plate;

a coupling gear fixedly attached to said second lead screw;

a coupling chain coupling said coupling gear of said first radial motion mechanism and said coupling gear of said second radial motion mechanism;

whereby said first radial motion mechanism and said second radial motion mechanism may be operated in tandem to move said second detector toward and away from the lateral axis.]

[7. An imaging system for acquiring imaging data generated by an object positioned about a lateral axis to form a SPECT image, said system comprising:

a main gantry body having left and right upright cylindrical walls each having an inner surface and an outer surface, said walls including a plurality of guide rollers rotatably attached to the inner surface of the walls at spaced apart radial positions;

first and second gamma ray detectors;

a first pair of rings located between said walls and oriented substantially perpendicular to and approximately centered on the lateral axis, each of said first pair of rings including a main cylindrical body having an inner face and an outer face, an outer radial flange integral with and perpendicular to an upper portion of said outer face and disposed towards and adjacent said gantry walls, and an L-shaped inner flange having a first member defining an upper radial support surface, said first member being integral with and perpendicular to a middle portion of said inner face, said L-shaped flange having a second member integral with and perpendicular to said first member and having one end proximate said lateral axis and having an integral upper lip extending above said radial support surface at the opposite end of the second member, wherein said outer flange defines a radial abutment undersurface for engaging said rollers attached to said walls of the main gantry body, and wherein said second member of said L-shaped inner flange and said inner face of said main cylindrical body define an inner radial groove therebetween;

a second pair of rings located between said walls and oriented substantially perpendicular to and approximately centered on the lateral axis, each of said second pair of rings having an inner face, an outer face, a side wall face, and a radial groove formed in the side wall face between the inner and outer face, wherein each of said rings includes a plurality of guide rollers rotatably mounted within the groove and extending slightly beyond said groove, said rollers radially spaced apart from each other around an inner surface of the groove for positioning each of said second rings upon said upper radial support surface of said first member of said L-shaped inner flange of each of said first pair of rings so that said second pair of rings is disposed between said first pair of rings and is rotatable along said radial support surface and is prevented from falling off of said surface by said upper lip of the second member of the L-shaped flange;

means for coupling said first and second detectors to said first and second pairs of rings respectively, with the first and second detectors pointed toward the lateral axis and disposed between said rings, said coupling means including means for moving the first and second detectors respectively toward and away from the lateral axis; and means for independently rotating said first and second detectors along a circular path approximately centered at said lateral axis.]

[8. An imaging system as claimed in claim 7 wherein said independent by rotating means includes a motor operatively coupled to first and second drive shafts, a pair of first and second drive gears fixedly attached to said first and second shafts, at least one pair of first and second idler gears operatively coupling said first and second drive gears to said first and second pairs of rings, and a braking means coupled to said second drive shaft;

wherein when said braking means is disengaged, the operation of the motor rotates said first and second shafts to thereby rotate said drive gears, said idler gears, and said rings and said detectors coupled thereto in a circular path approximately centered on the lateral axis, and wherein when said braking means is engaged, operation of said motor rotates only said first shaft so that rotation occurs only for said first gears and said first pair of rings to thereby adjust the angular displacement, relative to the lateral axis, between said first and second detectors to a predetermined magnitude.]

[9. An imaging system as claimed in claim 7 further comprising a plurality of adjustment blocks movably mounted to said gantry body walls and spaced radially apart from each other, each of said blocks having a guide roller rotatably fixed to the block and adapted to be positioned within the inner radial groove of said first pair of rings, wherein said adjustment blocks may be moved axially within said gantry walls substantially parallel to said lateral axis to thereby vary a lateral displacement of said first pair of rings from said gantry walls.]

*10. A medical imaging system for acquiring image data of an object, said system comprising:*

*a first pair of rotatable members rotatable about and substantially centered on a lateral axis;*

*a second pair of rotatable members rotatable about and substantially centered on a lateral axis;*

*a first radiation detector coupled to and disposed between the first pair of rotatable members; and*

*a second radiation detector coupled to and disposed between the second pair of rotatable members, the second pair of rotatable members movable with respect to the first pair of rotatable members so as to allow the angular displacement between the first and second detectors about the lateral axis to be varied.*

*11. A medical imaging system according to claim 10, wherein the first and second detectors are gamma radiation detectors.*

*12. A medical imaging system according to claim 10, wherein the first pair of rotatable members comprises a pair of ring-shaped members including a first ring-shaped member and a second ring-shaped member, and wherein the second pair of rotatable members comprises a pair of ring-shaped members including a third ring-shaped member and a fourth ring-shaped member.*

*13. A medical imaging system according to claim 10, wherein the second pair of rotatable members is disposed between the first pair of rotatable members.*

*14. An imaging system according to claim 10, wherein the angular displacement can be substantially any angle in a range from less than 90 degrees to approximately 180 degrees.*

*15. An imaging system according to claim 10, wherein each of the first and second radiation detectors includes a substantially planar surface, and wherein the imaging system further comprises first and second extended collimators mounted to the first and second radiation detectors, respectively, each of the first and second extended collimators having a collimator surface extending substantially beyond the planar surface of the corresponding detector.*

*16. An imaging system according to claim 15, wherein each of the first and second detectors comprises a beveled edge for reducing mechanical interference between the first and second detectors when the first and second detectors are oriented substantially perpendicular to each other.*

*17. An imaging system according to claim 10, further comprising:*

*means for rotating the first and second radiation detectors through a circular path centered substantially about the lateral axis to a plurality of angular positions to acquire the image data; and*

*means for varying the relative position of the object with respect to the first and second radiation detectors, vertically and horizontally with respect to the lateral axis, to substantially minimize the distance between the object and the first and second gamma ray detectors at each of the plurality of angular positions.*

*18. A medical imaging system for acquiring tomographic image data of an object, said system comprising:*

*a first pair of ring members rotatable about and substantially centered on a lateral axis;*

*a second pair of ring members rotatable about and substantially centered on a lateral axis and disposed between the first pair of ring members;*

*a first gamma ray detector coupled to and disposed between the first pair of ring members; and*

*a second gamma ray detector coupled to and disposed between the second pair of ring members, the second pair of ring members rotatable with respect to the first pair of ring members so as to allow the angular displacement between the first and second gamma ray detectors about the lateral axis to be varied.*

*19. An imaging system according to claim 18, wherein the angular displacement can be substantially any angle in a range from less than 90 degrees to approximately 180 degrees.*

*20. An imaging system according to claim 18, wherein each of the first and second gamma ray detectors includes a substantially planar surface, and wherein the medical imaging system further comprises first and second extended collimators mounted to the first and second gamma ray detectors, respectively, each of the first and second extended collimators having a collimator surface extending substantially beyond the planar surface of the corresponding detector.*

*21. A medical imaging system according to claim 18, wherein each of the first and second gamma ray detectors comprises a beveled edge for reducing mechanical interference between the first and second gamma ray detectors when the first and second gamma ray detectors are oriented substantially perpendicular to each other.*

*22. An imaging system according to claim 18, further comprising:*

*means for rotating the first and second gamma ray detectors through a circular path centered substantially about the lateral axis to a plurality of angular positions to acquire the image data; and*

*means for varying the relative position of the object with respect to the first and second gamma ray detectors, vertically and horizontally with respect to the lateral axis, to substantially minimize the distance between the object and the first and second gamma ray detectors at each of the plurality of angular positions.*

* * * * *